United States Patent
Graumann

(10) Patent No.: US 9,468,415 B2
(45) Date of Patent: Oct. 18, 2016

(54) COUPLING UNIT AND METHOD FOR DETERMINING AN ALIGNMENT OF THE COUPLING UNIT

(71) Applicant: SIEMENS AKTIENGESELSCHAFT, Munich (DE)

(72) Inventor: Rainer Graumann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 82 days.

(21) Appl. No.: 14/499,475

(22) Filed: Sep. 29, 2014

(65) Prior Publication Data

US 2015/0093180 A1    Apr. 2, 2015

(30) Foreign Application Priority Data

Sep. 27, 2013    (DE) .................. 10 2013 219 592

(51) Int. Cl.
| | | |
|---|---|---|
| *G01B 5/008* | (2006.01) | |
| *A61B 6/00* | (2006.01) | |
| *A61B 6/04* | (2006.01) | |

(52) U.S. Cl.
CPC ............. *A61B 6/547* (2013.01); *A61B 6/4458* (2013.01); *A61B 6/0407* (2013.01); *A61B 6/4405* (2013.01); *A61B 6/4441* (2013.01); *Y10T 403/1624* (2015.01)

(58) Field of Classification Search
CPC .................................................... G01B 5/008
USPC ......................................... 33/503, 613, 645
See application file for complete search history.

(56) References Cited

U.S. PATENT DOCUMENTS

| | | | | |
|---|---|---|---|---|
| 5,829,148 A * | 11/1998 | Eaton | ..................... | G01B 5/008 33/1 PT |
| 2004/0015053 A1* | 1/2004 | Bieger | ............... | A61B 1/00149 600/117 |
| 2005/0151963 A1* | 7/2005 | Pulla | ...................... | G01B 21/04 356/139.03 |
| 2005/0166413 A1* | 8/2005 | Crampton | ............. | B25J 13/088 33/503 |
| 2007/0165775 A1* | 7/2007 | Graumann | ........... | A61B 6/4441 378/19 |
| 2008/0204864 A1 | 8/2008 | Sander | | |
| 2009/0271996 A1* | 11/2009 | Ferrari | ................. | G01B 21/042 33/502 |
| 2014/0086393 A1* | 3/2014 | Graumann | ........... | A61B 6/4441 378/198 |
| 2014/0190027 A1* | 7/2014 | Abe | ....................... | G01B 5/008 33/503 |
| 2014/0324182 A1* | 10/2014 | Graumann | ............ | A61B 19/50 623/22.12 |
| 2015/0345933 A1* | 12/2015 | Nagataki | .............. | G01B 11/007 33/503 |
| 2015/0362305 A1* | 12/2015 | Ferrari | ................... | G01B 5/012 33/503 |

FOREIGN PATENT DOCUMENTS

DE    102007009543 A1    8/2008

* cited by examiner

*Primary Examiner* — G. Bradley Bennett
(74) *Attorney, Agent, or Firm* — Laurence Greenberg; Werner Stemer; Ralph Locher

(57) ABSTRACT

First and second equipment units are connected to a coupling unit configured with angle and/or position sensors in order to determine thereby, for example, a relative position of a first equipment unit in relation to a second equipment unit. In this manner alignment of the first and second equipment units is expedited.

8 Claims, 1 Drawing Sheet

COUPLING UNIT AND METHOD FOR DETERMINING AN ALIGNMENT OF THE COUPLING UNIT

CROSS-REFERENCE TO RELATED APPLICATION

This application claims the priority, under 35 U.S.C. §119, of German application DE 10 2013 219 592.3, filed Sep. 27, 2013; the prior application is herewith incorporated by reference in its entirety.

BACKGROUND OF THE INVENTION

Field of the Invention

The invention relates to an apparatus and a method for positioning equipment units.

Equipment units, in particular mobile medical equipment units, are moved up to an examination region and aligned there manually or in an electronically controlled manner for diagnostic purposes. A mobile C bow is an example of a diagnostic device. After taking an individual X-ray or a sequence thereof, the C bow is moved from the position of use to a parking position within or at a location adjacent to the treatment space. In order to take further X-rays, the mobile C bow is moved back to its position of use so as to enable the documentation of treatment progress and/or the course of operations, or further approaches to treatment for surgical interventions. A repeated use of the mobile C bow entails the problem that the C bow must be repositioned manually.

It has been usual to date for the assistant or the treating doctor himself to position the mobile X-ray machine at the patient and align it with the latter manually. In addition to a possible contamination of a region that is to be kept sterile around the zone of the intervention, this entails the additional disadvantage that, because of inaccurate knowledge concerning the location and orientation of the zone that is to be imaged again, it is necessary to repeat an X-ray and thereby lay the patient open to an unnecessary exposure to radiation.

SUMMARY OF THE INVENTION

It is accordingly an object of the invention to provide an apparatus and a method for positioning equipment units that overcome the above-mentioned disadvantages of the prior art devices and methods of this general type.

With the foregoing and other objects in view there is provided, in accordance with the invention, a coupling unit. The coupling unit contains a first docketing element, a second docking element and at least one coupling element having a position detecting element and disposed between the first and second docking elements. It is possible to determine a position and/or alignment of the first and second docking elements in conjunction with docking points of a first and/or second equipment unit.

The apparatus and the associated method have a coupling unit with a coupling element, and a first and second docking element. In one variant embodiment, at least one connecting element and an articulation element with at least one position detecting element are arranged in the coupling element, it being possible to use the elements to determine the relative position and/or alignment of the first and second docking elements in conjunction with at least one docking point, at a first and/or second equipment unit, that is operationally connected via the first and/or second docking element.

The invention is attended by the advantage that, first, a position of an equipment unit in relation to a further equipment unit can be detected exactly and, second, the equipment unit can be repositioned again with the aid of the stored position data.

The invention is attended by the advantage that an equipment unit can be repositioned without an additional navigation system.

The invention is attended by the advantage that, owing to the targeted repositioning of a C bow, further X-rays of the zone of intervention are accomplished quickly and exactly, and no unnecessary X-ray results from poor X-rays.

In accordance with an added feature the invention, the coupling element is formed from at least one glass fiber element with laser coupling and laser decoupling for position detection.

In accordance with another feature of the invention, the coupling element has at least one connecting element with at least one articulation element, and in that the connecting element and/or the articulation element has the position detecting element.

In accordance with an additional feature of the invention, the position detecting element is an angle and/or position sensor.

In accordance with a further feature of the invention, the coupling element has a first connecting element and an articulation element with at least one degree of freedom on both sides in each case. The articulation element is one of a plurality of articulation elements; and the coupling element has a second and a third connecting element. The second and third connecting elements are respectively connected to one of the articulation elements.

In accordance with yet another feature of the invention, the first equipment unit is assigned a first arithmetic logic unit and the second medical equipment unit is assigned a second arithmetic logic unit. The first and second arithmetic logic units are configured such that the first and second arithmetic logic units respectively interrogate sensor data of the position detecting element, and an alignment of the coupling unit is determined in the first and/or second arithmetic logic unit.

With the foregoing and other objects in view there is provided, in accordance with the invention, a method for determining an alignment of a coupling unit having a first and second docking element. The method includes the step of determining a position and/or alignment of the first and second docking elements in conjunction with first and second docking points of a first and/or second equipment unit.

Other features which are considered as characteristic for the invention are set forth in the appended claims.

Although the invention is illustrated and described herein as embodied in a coupling unit and a method for determining an alignment of the coupling unit, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
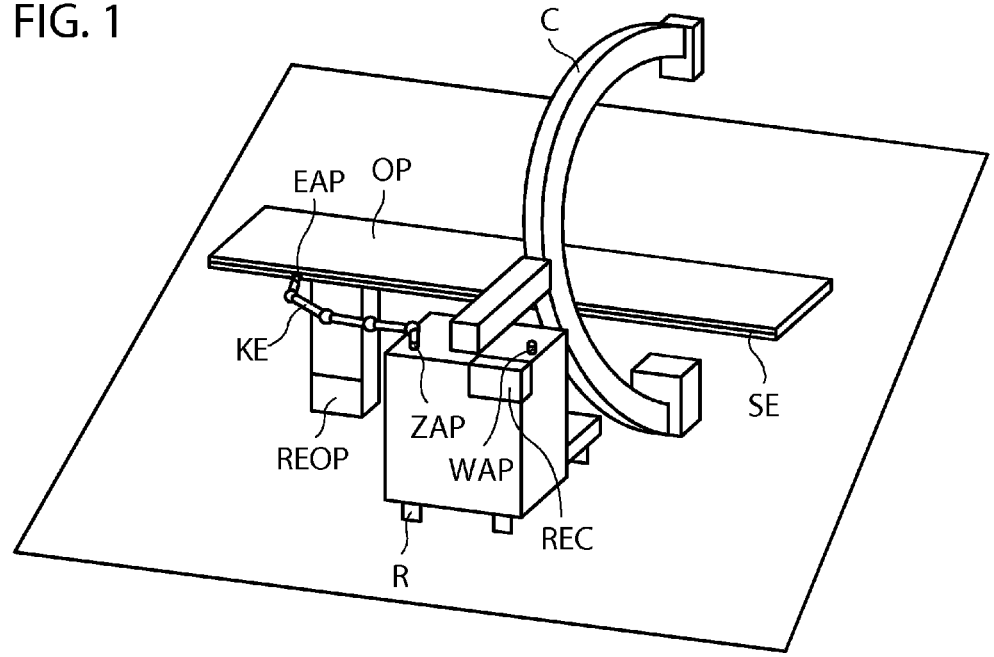
FIG. 1 is a diagrammatic, perspective view of a coupling unit in a use position between two medical equipment units according to the invention.

Referring now to the figures of the drawings in detail and first, particularly to FIG. 1 thereof, there is shown first and second equipment units C, OP connected to a coupling unit KE configured with angle and/or position sensors in order to determine thereby, for example, a relative position of the first equipment unit C in relation to the second equipment unit OP.

FIG. 1 shows in a schematic view a section of a treatment space with the first and second equipment units C, OP. In the example, the first equipment unit is a mobile C bow C, and the second equipment unit is an operating table OP. A lying area of the operating table OP can be varied in alignment, inclination and/or height setting as desired. The mobile C bow C, which is displaceable on wheels R, can likewise be positioned freely in the treatment space and in relation to the patient. When they are grouped in the immediate vicinity of one another, the mobile C bow C and the operating table OP are connected to the coupling unit KE. The operating table OP has at least one defined first interface, denoted as a first docking point EAP, and the mobile C bow C likewise has at least two defined interfaces denoted as a second and a further docking point ZAP, WAP. Along a rail running at a side of the lying area of the operating table OP, the first docking point EAP can be latched and/or positioned as desired on the rail. The rail can surround parts of the lying area, or all the lying area. A docking point on the mobile C bow C can also, however, be achieved via rail elements; the calculation of the docking point is performed as in the case of the determination of the docking point in the case of the operating table OP.

Figure 2:
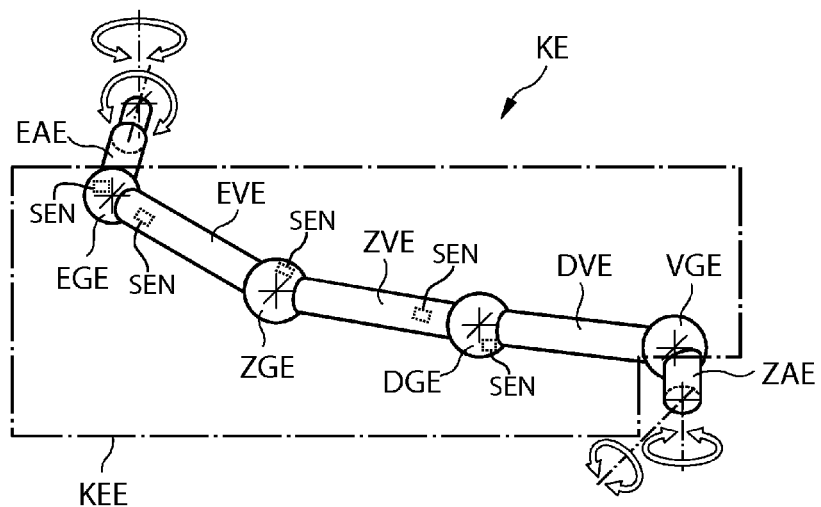
FIG. 2 is a diagrammatic, perspective view of the coupling unit.

A configuration of the coupling unit KE with a coupling element KEE is illustrated in FIG. 2. At its first end, the coupling unit KE has a first docking element EAE, and at its second end it has a second docking element ZAE. The coupling element KEE is connected to the first docking point EAP on the operating table OP with the aid of the first docking element EAE, and is connected to the second docking point ZAP on the mobile C bow C with the aid of the second docking element ZAE. The coupling element KE is configured with at least one first connecting element EVE between the docking elements EAE, ZAE. The docking elements EAE, ZAE are connected to the connecting element EVE via an articulation element EGE, VGE respectively. In the variant embodiment, the first connecting element EVE is extended with the aid of a second and a third connecting element ZVE, DVE. A second articulation element ZGE is integrated between the first and second connecting elements EVE, ZVE, and a third articulation element DGE is integrated between the second and third connecting elements ZVE, DVE. The articulation elements respectively have at least one degree of freedom. Angle and/or position sensors SEN are arranged in the coupling unit KE for the relative determination of the orientation and alignment of the connecting elements and/or the articulation elements of the coupling unit KE. The operating table OP is configured with a second arithmetic logic unit REOP, and the mobile C bow C is configured with a first arithmetic logic unit REC. The position of the first docking point EAP, positioned on the operating table, can be determined with the aid of the second arithmetic logic unit REOP and stored. The determination of the position can be performed, for example, by use of resistance measurement or via a matrix integrated in the rail SE. The position of the second and of the further docking points ZAP, WAP is stored in the first arithmetic logic unit REC assigned to the mobile C bow. The first arithmetic logic unit REC in the mobile X-ray unit C is configured in such a way that, after a connection of the two equipment units OP, C by the coupling unit KE, it interrogates the position of the docking point EAP on the operating table OP by cable or radio connection, and includes the position in the calculations for the alignment of the C bow in relation to the operating table OP. Proceeding from the position and alignment of the first docking point EAP, the sensor data of the angle sensors and/or position sensors SEN in the connecting elements and/or articulation elements are interrogated and calculated with the aid of the dimensioning prescribed by the connecting and articulation elements, and the geometry. Depending on the starting point EAP, ZAP, the result is the position and alignment of the first and/or second docking element EAE, ZAE. After the connection of the docking points EAP, ZAP to the first or second docking element EAE, ZAE, the relative positioning of the C bow in relation to the lying area of the operating table is available.

In order to take an X-ray, the mobile C bow C is pushed or moved toward the patient lying on the operating table OP. In order to determine the position of the mobile C bow C with reference to the operating table and thus also to the patient, the two devices are connected by the coupling unit KE. In order to detect the position of the C bow C, the coupling unit KE is connected to the operating table OP with its first end at the first docking point EAP, and is connected to the mobile C bow C with its second docking element ZAE, located at the second end, with a docking point. The first docking point EAP is a point on a rail-shaped element on the edge of the operating table OP. The second docking point ZAP or a further docking point WAP is arranged on the mobile C bow C. The second and further docking points ZAP, WAP present a defined point on the mobile C bow C. The exact orientation of the first docking point EAP plugged into the rail element can be determined by an electrical, magnetic or optical measurement after the first docking element EAE has been plugged in. The second or further docking point ZAP, WAP on the mobile medical device is known respectively to the first and second arithmetic logic units REC, REOP.

The alignment data determined are stored by the first arithmetic logic unit REC of the mobile C bow C, for example in a patient data file. The data can also be calculated, for example, with the aid of an optical navigation system arranged in the operating space and having marker-based determinations of position. In relation to a repositioning, the stored data relating to the position and alignment of the mobile C bow C are fed again to the first arithmetic logic unit REC in the mobile C bow C. The repositioning of the mobile C bow C is performed under computer control with the aid of a display arranged on the mobile C bow, for example. The operator is guided to the stored starting point by indications of direction on the display.

Once the mobile C bow has been positioned and the position and alignment of the docking elements EAE, ZAE and of the at least one connecting element EVE have been stored or buffered, the relative position of the mobile C bow C in relation to the operating table OP, and/or the absolute position of the mobile C bow C in the case of further data relating to the location of the operating table OP can be determined and displayed. In order, in addition, to determine the absolute position of the operating table OP and/or of the mobile C bow C, the first and second computers REC, REOP know of the position of the operating table OP or the position of the mobile C bow C, for example via an optical or electromagnetic tracking system.

In a further configuration, instead of the configuration of the coupling unit KE with angle and/or position sensors, it is possible to use a flexible tube having at least one laser light guided in a glass fiber with rigid end pieces. In this configuration, at least one position detecting system which determines the bend of the glass fiber is integrated in the tube.

The coupling unit KE can, for example, also be used to determine the relative position of a robot system in relation to the operating table. The use of the coupling unit KE is not limited to a mobile C bow C or a couch unit OP.

The following is a summary list of reference numerals and the corresponding structure used in the above description of the invention:
C First equipment unit/C bow/mobile medical device
OP Second equipment unit/operating table
REC First arithmetic logic unit in the mobile medical device
REOP Second arithmetic logic unit in the operating table
SE Rail element
EAP First docking point
ZAP Second docking point
WAP Further docking point
R Wheels
KE Coupling unit
KEE Coupling element
EAE First docking element
ZAE Second docking element
EVE First connecting element
ZVE Second connecting element
DVE Third connecting element
EGE First articulation element
ZGE Second articulation element
DGE Third articulation element
VGE Fourth articulation element
SEN Angle and/or position sensor

The invention claimed is:

1. A coupling unit, comprising:
a first docking element configured for attaching to a first docking point on a first equipment unit;
a second docking element configured for attaching to a second docking point on a second equipment unit; and
at least one coupling element having a position detecting element and disposed between said first and second docking elements, it being possible to determine a position and/or alignment of said first and second docking elements in conjunction with the first and second docking points of the first and/or second equipment unit.

2. The coupling unit according to claim 1, wherein said coupling element is formed from at least one glass fiber element with laser coupling and laser decoupling for position detection.

3. The coupling unit according to claim 1, wherein said coupling element has at least one connecting element with at least one articulation element, and in that said connecting element and/or said articulation element has said position detecting element.

4. The coupling unit according to claim 1, wherein said position detecting element is an angle and/or position sensor.

5. The coupling unit according to claim 1, wherein said coupling element has a first connecting element and an articulation element with at least one degree of freedom on both sides in each case.

6. The coupling unit according to claim 5, wherein:
said articulation element is one of a plurality of articulation elements; and
said coupling element has a second and a third connecting element, and said second and third connecting elements are respectively connected to one of said articulation elements.

7. The coupling unit according to claim 1, wherein the first equipment unit is assigned a first arithmetic logic unit and the second equipment unit is assigned a second arithmetic logic unit, the first and second arithmetic logic units configured such that said first and second arithmetic logic units respectively interrogate sensor data of said position detecting element, and an alignment of the coupling unit is determined in the first and/or second arithmetic logic unit.

8. A method for determining an alignment of a coupling unit having a first and second docking element, which comprises the steps of:
connecting the first docking element to a first docking point on a first piece of equipment;
connecting the second docking element to a second docking point on a second piece of equipment; and
determining a position and/or alignment of the first and second docking elements in conjunction with the first and second docking points of the first and/or second piece of equipment.

* * * * *